US011253245B2

(12) United States Patent
Green et al.

(10) Patent No.: US 11,253,245 B2
(45) Date of Patent: Feb. 22, 2022

(54) ILLUMINATED SUCTION RETRACTOR DEVICE

(71) Applicant: University of Virginia Patent Foundation, Charlottesville, VA (US)

(72) Inventors: Megan E. Green, Fairfax, VA (US); Madeline M. Morris, New York, NY (US); Maria Filippa Trikantzopoulou, Charlottesville, VA (US); Patrick S. Cottler, Charlottesville, VA (US); Jonathan S. Black, Crozet, VA (US); Anthony J. Archual, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 15/968,096

(22) Filed: May 1, 2018

(65) Prior Publication Data
US 2018/0317902 A1    Nov. 8, 2018

Related U.S. Application Data

(60) Provisional application No. 62/500,830, filed on May 3, 2017.

(51) Int. Cl.
*A61B 17/02* (2006.01)
*A61B 90/30* (2016.01)
(Continued)

(52) U.S. Cl.
CPC .......... *A61B 17/0231* (2013.01); *A61B 17/02* (2013.01); *A61B 17/0218* (2013.01); *A61B 90/30* (2016.02); *A61B 2017/00862* (2013.01); *A61B 2017/00867* (2013.01); *A61B 2017/00946* (2013.01); *A61B 2017/0225* (2013.01); *A61B 2090/308* (2016.02); *A61B 2217/005* (2013.01); *A61F 2002/2878* (2013.01)

(58) Field of Classification Search
CPC ............ A61B 17/0231; A61B 17/0281; A61B 17/0206; A61B 17/02; A61B 17/0218; A61B 2017/0225; A61B 2017/0287; A61B 2017/0212
USPC ........................................................ 600/236
See application file for complete search history.

(56) References Cited

U.S. PATENT DOCUMENTS 3,626,471 A    12/1971 Florin
6,059,723 A    5/2000 Davis
(Continued)

FOREIGN PATENT DOCUMENTS

EP    2201899 A1 *  6/2010    ......... A61B 17/0231

OTHER PUBLICATIONS

Allareddy et al., "Epidemiology of Facial Fracture Injuries", Journal of Oral and Maxillofacial Surgery, 2011, pp. 2613-2618, vol. 69, No. 10, American Association of Oral and Maxillofacial Surgeons.
(Continued)

*Primary Examiner* — Amy R Sipp
(74) *Attorney, Agent, or Firm* — Robert J. Decker

(57) ABSTRACT

A surgical device for retracting tissue of a subject while offering lighting and suction means integrated into the same device. This device is useful in many different surgical procedures, including those requiring precise tissue retraction in small openings of a subject, such as facial orbital fracture repair.

10 Claims, 13 Drawing Sheets

(51) Int. Cl.
A61B 17/00 (2006.01)
A61F 2/28 (2006.01)

(56) References Cited

U.S. PATENT DOCUMENTS

| | | |
|---|---|---|
| 6,468,206 B1 | 10/2002 | Hipps |
| 6,482,153 B1 | 11/2002 | Hipps |
| 7,306,559 B2 | 12/2007 | Williams |
| 7,951,077 B2 | 5/2011 | Sayeg |
| 8,795,162 B2 | 8/2014 | Vayser |
| 9,510,737 B2 | 12/2016 | Vayser |
| 2006/0247500 A1* | 11/2006 | Voegele ............. A61B 17/3417 600/208 |
| 2015/0025324 A1 | 1/2015 | Wan |
| 2018/0228483 A1* | 8/2018 | Duggal .................. A61B 90/30 |

OTHER PUBLICATIONS

Doctor Stock, Left Orbital Fractures, (n.d.), 1 page.
Hwang et al., "Analysis of facial bone fractures: An 11-year study of 2,094 patients", Indian Journal of Plastic Surgery, 2010, pp. 42-48, vol. 43, No. 1.
Mok et al., "A review of materials currently used in orbital floor reconstruction", The Canadian Journal of Plastic Surgery, 2004, pp. 134-140, vol. 12, No. 3.
Short Notes in Plastic Surgery, "33. Blowout Fracture of the Orbit", Apr. 15, 2013, 7 pages, from https://shortnotesinplasticsurgery.wordpress.com/2013/04/15/735/.

* cited by examiner

ILLUMINATED SUCTION RETRACTOR DEVICE

RELATED APPLICATIONS

The present application claims benefit of priority under 35 U.S.C § 119 (e) from U.S. Provisional Application Ser. No. 62/500,830, filed May 3, 2017, entitled "Orbital Floor Malleable Retractor Device and Related Method"; the disclosure of which is hereby incorporated by reference herein in its entirety.

FIELD OF INVENTION

The present disclosure relates generally to a medical device and the operation of said device. More particularly, a device for the retraction of tissue of a subject's anatomical region while providing suction and illumination in the same device while also in a plurality of positions, contours, and configurations. This device is useful in a wide array of surgical procedures including orbital fracture repair.

BACKGROUND

One of the most common fractures of the midface is an orbit fracture. Orbital fractures are the result of energy transmitted in the form of pressure or through direct mechanical stress to the orbital walls, including the medial wall and/or the orbital floor. The most common circumstances of orbital floor fracture include violent assaults, falls, and motor vehicle accidents.

Trauma to an orbital wall creates an opening under a patient's globe which releases fat and other orbital contents that can herniate, thereby increasing the orbital volume. Literature supports a linear correlation between increased orbital floor volume and degree of enophthalmos, which is posterior displacement of the eye. Suction tools are used to resist increases in orbital volume. Inflammation and edema are expected sequelae of soft tissue trauma, both create a dilemma for a treating clinician because they mask increases in orbital volume. Although not all facial fracture cases will have an orbital floor fracture it is encouraged to explore the orbital floor to minimize the aforementioned risks.

The main challenges for orbital floor repair are surgical timing, approach, and choice of material for reconstruction. Currently, surgeons rely on separate tools and a team to repair an orbital floor. During the hour-long surgery, suction and lighting must be provided by additional nurses and residents in order to combat the accumulation of blood and intraocular fluid in the poorly lit space. The physician must rely on others in order to work effectively. Multiple tools and hands in the orbital space hinders operational efficiency.

There is a need for a device to facilitate visibility in difficult-to-see surgical cavities that provides surgeons full autonomy of orbital floor fracture repairs and other medical procedures. The challenges described above will be overcome by the embodiments disclosed herein.

SUMMARY OF ASPECTS OF EXEMPLARY EMBODIMENTS OF THE INVENTION

An aspect of an embodiment provides for surgical tools and more specifically to a surgical tool with an integrated suction and illumination abilities that at the same time can provide for a plurality of positions, contours, and configurations.

The devices described below provide an improved option for illumination and suction to be provided during a medical process requiring retraction. Examples of a relevant procedure include orbital fracture repair, brain surgery, oral surgery, various procedures by pediatric surgeons, spinal repair, and the like. To further assist in these procedures the devices described below may be combined with a variety of other medical tools to offer greater efficiencies. These medical tools may include items for facial or other bodily trauma such as plates, screws, scalpels, and other retractors, cautery tools, implants, devices for delivery of implants, or any similar tool or item that would assist a user. The retraction device described below includes a metal or non-metallic elongated member with a proximal end and a distal end connected by a central portion of said elongated member. Attached to or in communication with this elongated member are a suction means and an illumination means.

An exemplary embodiment of this elongated member is comprised of steel. Steel offers an ideal bend modulus, being able to be bent by the user but not substantively deforming when used to retract tissue during the procedures. Strength, workability, and lack of recoil are all features that need to be satisfied in the selection of a material in aspects of various embodiments of the present invention. Additionally as some embodiments may be designed to be reused, steel solves this problem by offering ease of sterilization, a major concern for medical procedures.

Other embodiments of this elongated member may be comprised of materials possessing a significantly lower modulus of elasticity, such as tin, tin alloys, nickel, copper, etc. These materials may be more useful for a user who wants to be able to more finely adjust the elongated member. Other embodiments of this elongated member may be comprised of materials possessing a significantly higher modulus of elasticity. These materials may be more useful for a user who wants to be able to more rigorously adjust the elongated member.

In an aspect of an embodiment, the suction means may be a suction tube or multiple tubes (or other types of channels) that are attached onto or in communication with the elongated member (or onto other components of the retractor device). In an embodiment, this tubing can be metal or non-metal and has a proximal and distal end that may align with the proximal and/or distal end of the elongated member to which it is attached. In an embodiment, this tubing may run the length of the elongated member but may end before the distal end of the elongated member creating a setoff. By ending before the end of the distal edge of the elongated member this allows for the tubes to continue to provide suction with a reduced risk of being plugged by tissue in the anatomical region.

In some embodiments these tubes are secured in place by retainers, such as clips, at or proximal to the setoff location. In other embodiments these retainers, while they hold the suction tubes in place during the procedure, allow the suction tubes to be adjusted and moved into the appropriate position by the user. This allows the device to be adaptable to each individual subject's anatomy and situation.

An aspect of an embodiment of the retractor device is to additionally provide lighting to the subject's anatomical region as desired or required. It may do this via light sources positioned on the distal end of the elongated member. This retractor remaining flexible is important, thus a light source such as an LED or series of LED lights may be positioned along this distal end to allow the retractor to still be bent to the desired shape. In an alternate configuration these light sources may be placed on opposite sides of the elongated member, which would allow for illumination of the entirety of the anatomical region or other predetermined area of the anatomical regions as desired or required.

Current retractor devices have been constructed to be thin strips of metal which are only capable of retracting tissue. As such this means that multiple other tools are required to assist during surgery when operating current retractor devices. During current practices, assistance during surgical procedures with one or more other hands (users such as clinicians) is needed to operate tools providing light and tools providing suction. As many different tools are needed during current practices for a single procedure this then drastically lengthens the required time and complexity for these procedures, and causes inefficiencies.

An aspect of an embodiment of the present invention device allows suction, lighting, and retraction features to be integrated on the same retractor while having the retractor still able to be bent yet withstand bending due to forces imposed by the subject's tissues to the level necessary. The device does this while continuing to provide suction and light throughout the needed bending and twisting through the desired range of angles covering multiple planes. Especially in orbital fracture repair where the orbital floor is approximately 5 millimeters from the optic nerve, the precise bending coupled with the lighting and suction capabilities offer efficiencies and safety. These efficiencies reduce clinician labor while providing superior lighting, suction, and maneuverability in the anatomical region.

An aspect of an embodiment of the present invention provides, among other things, a retractor device for accessing an anatomical region of a subject. The retractor may comprise: an elongated member having a distal end and a proximal end with a longitudinal segment extending there between, wherein the distal end of the elongated member is configured to access the anatomical region; one or more tubes capable of providing suction, the one or more tubes disposed on the elongated member and the one or more tubes include a distal aperture, wherein distal apertures of the tubes are located at or proximate to the distal end of the elongated member, and the distal apertures are configured to provide the suction to the anatomical region; one or more light sources coupled to the elongated member, the light sources capable of providing light, and the light sources configured to provide lighting to the anatomical region; and the longitudinal member of the elongated member is configured to be bent in one or more positions in response to manual forces that may be applied by a user onto the elongated member, and wherein the tubes remain operable to provide suction in the one or more bent positions and the light sources remain operable to provide light in the one or more bent positions.

An aspect of an embodiment of the present invention provides, among other things, a device for accessing an anatomical region of a subject. The device may comprise: a retraction means for accessing the anatomical region of a subject, wherein the retraction means is configured to be bent in one or more positions in response to forces that may be applied by a user onto the retraction means; a suction means for providing suction to the anatomical region; a lighting means for providing light to the anatomical region; and wherein the retraction means, suction means, and lighting means are capable of being provided simultaneously while the retraction means is bent in the one or more positions.

An aspect of an embodiment of the present invention provides, among other things, a medical device and the operation of the device. An aspect of an embodiment provides a device for the retraction of tissue of a subject's anatomical region while providing suction and illumination in the same device while also in a plurality of positions, contours, and configurations. An aspect of an embodiment of the device is useful in a wide array of surgical procedures including, but not limited thereto, orbital fracture repair.

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The invention itself, together with further objects and attendant advantages, will best be understood by reference to the following detailed description, taken in conjunction with the accompanying drawings.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
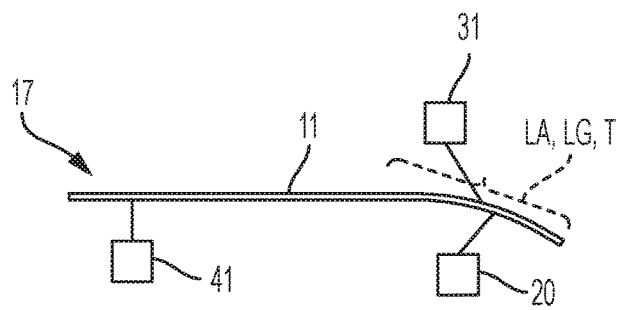
FIG. 1 schematically illustrates an exemplary embodiment of the retractor showing elongated member with suction means, light source, and power supply that is capable of being bent longitudinally, LG, bent laterally, LA, or twisted, T.
Figure 14:
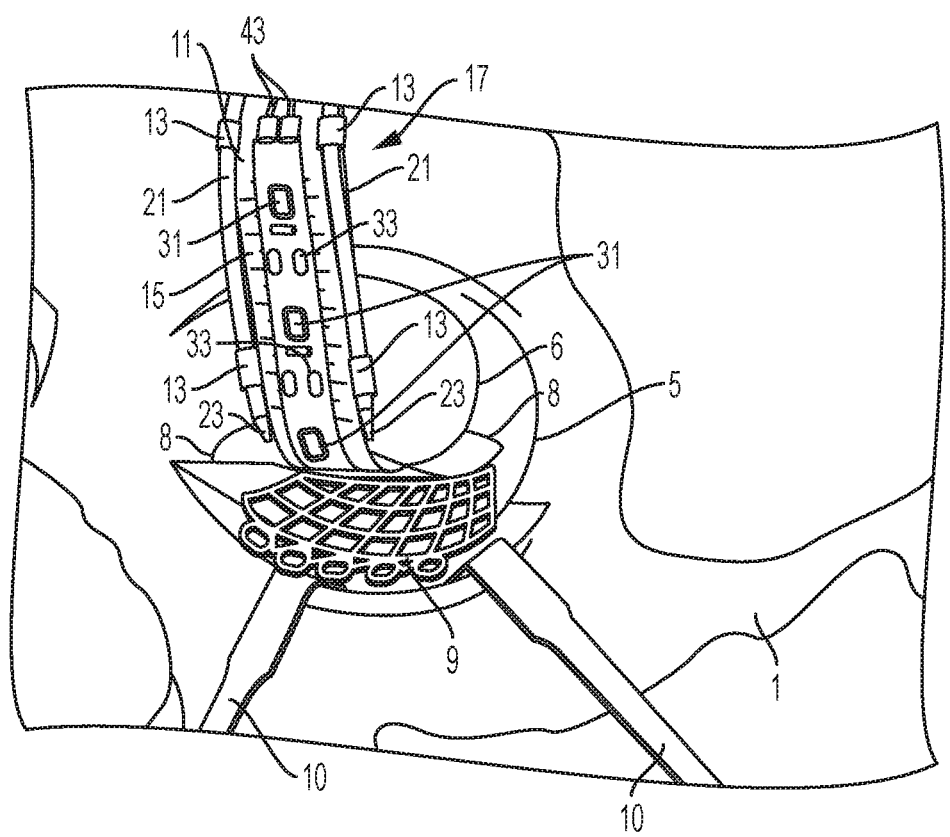
FIG. 14 schematically illustrates a user using the retractor device and the insertion of reconstructive material in a subject's orbital cavity.

Referring to FIG. 1 retractor device 17 includes a suction means 20 and lighting means 30 attached to elongated member 11. The retractor device may also be connected, either locally or remotely, to a power source 41. The elongated member 11 in this embodiment or any of the embodiments disclosed herein may be made of any suitable material or combination of materials such as metal like steel, stainless steel, titanium, copper, tin, or nickel, shape-memory alloy (SMA), or non-metal such as rubber, plastic, injection moldable plastic, other polymers, and the like that can bend with pressure from the hand of a user but retain its position against tissue of a subject during use. An exemplary embodiment of this material or combination of materials may have a modulus of elasticity or Young's modulus in the range of about 60 GPa to about 250 GPa which may allow for the proper bending capabilities of the elongated member 11. This material may be capable of being bent in one or more subsequent positions in response to the aforementioned manual forces of a user. In addition it may be capable of not substantially bending in response to forces from the accessing of the anatomical region or the retraction of tissue of a subject 1 (as illustrated in FIG. 14, for example). This bending of the elongated member 11 and/or related components of the retractor device 17 by a user may take place one or more times along the longitudinal axis, AG, in the longitudinal direction, along the lateral axis, AA, in the lateral direction, or both the longitudinal and lateral directions (which would amount to twisting).

Figure 8:
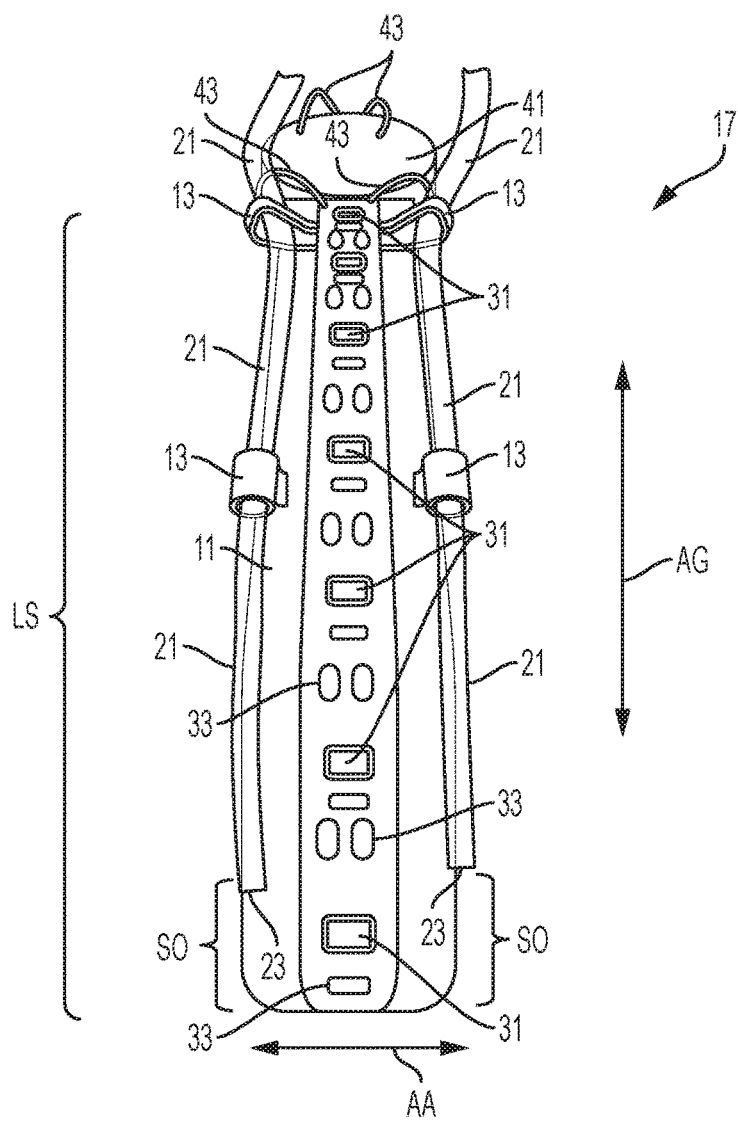
FIG. 8 is another perspective view which schematically illustrates another embodiment of a retractor with lighting and suction capabilities.

Light source 31 in this embodiment or any of the embodiments disclosed herein may be any light producing item or collection of multiple items. The light source 31 may be any light device, instrument, hardware, or component. This includes, for example, light emitting diodes (LED), fiber optic, and the like. In some embodiments this may be a series or collection of light sources while in other embodiments this may be a singular light source. As surgeons or users may need lights in different areas these light sources may be placed in various locations on any side and on any number of sides of the elongated member along the entire longitudinal span, LS, (See for example FIGS. 8 and 10) of the elongated member 11, utilizing any number of lights sources, in this or any other embodiments disclosed herein. This allows for optimal lighting in an anatomical region. This is further illustrated in FIGS. 16-20, for example.

In FIG. 1 the suction means in this embodiment or any other disclosed herein may consist of one or more tubes. These tubes may be made of any suitable material such as a metal, stainless steel or aluminum for example, or polymer such as PVC, ABS, or other similar materials. The cross sections of the suction means for this or any embodiment may be circular, non-circular, rectangular, D-shaped, or any other geometry.

Additionally, these tubes may be adjustable or secured in a designated place in this or other embodiments described herein. The distal end of these suction tubes ends in an aperture 23 which may be aligned with the distal end of the elongated member, such as in FIG. 7, positioned to end before the distal end of the elongated member which creates a setoff SO, such as in FIG. 8, or positioned to extend beyond the distal end of the elongated member (not shown). Moreover, the retractor device 17 may be comprised of a variety of materials and structures to provide for malleability that may allow for the flexion of the elongated member such as twisting (See, for example, FIGS. 17-20) so as to including longitudinal bending, LG, along the longitudinal axis, AG, and lateral bending, LA, along the lateral axis, AA.

As surgeons or users may need suction provided in different areas the suction tube or tubes 21 may be placed in various locations, along the entire longitudinal span, LS, of the elongated member 11 (See for example FIGS. 8 and 10), on any side and on any number of sides of the elongated member 11 (or various locations on any of the related components of the retractor device 17), utilizing any number of suction tubes, in this or any other embodiments disclosed herein. This allows for optimal suction in an anatomical region.

Figure 2:
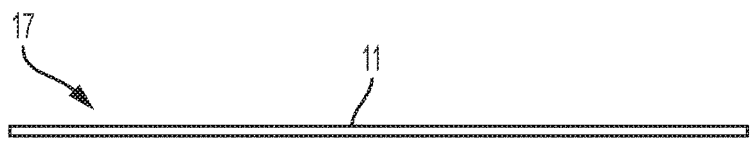
FIG. 2 schematically illustrates a cross section view (side view) of a non-bent elongated member.

FIG. 2 schematically illustrates a cross section view (side view) of a non-bent elongated member.

Figure 3:
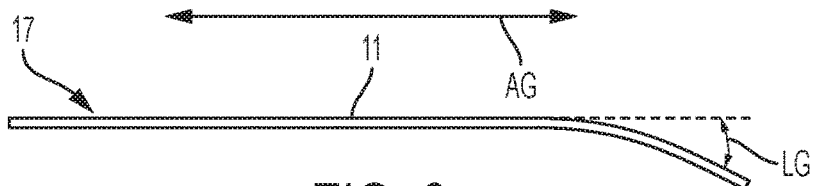
FIG. 3 schematically illustrates a cross section view (side view) wherein the elongated member has been bent in the longitudinal direction along the longitudinal axis, AG.

FIG. 3 schematically illustrates a cross section view (side view) wherein the elongated member has been bent longitudinally, LG, in the longitudinal direction along the longitudinal axis, AG as schematically indicated by angle, LG.

Figure 4:
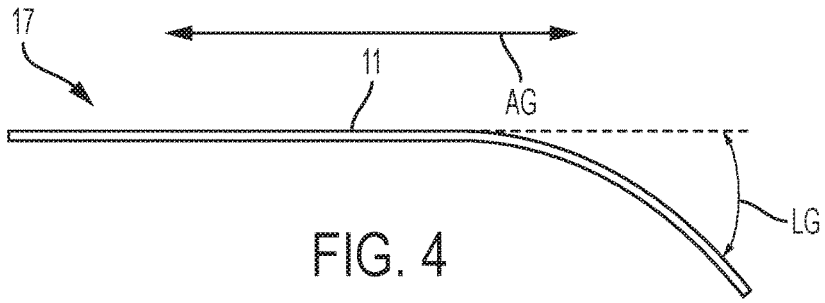
FIG. 4 schematically illustrates a cross section view (side view) wherein the elongated member has been further bent in the longitudinal direction along the longitudinal axis, AG.

FIG. 4 schematically illustrates a cross section view (side view) wherein the elongated member has been further bent longitudinally, LG, (compared to FIG. 3) in the longitudinal direction along the longitudinal axis, AG as schematically indicated by angle, LG.

Figure 5:
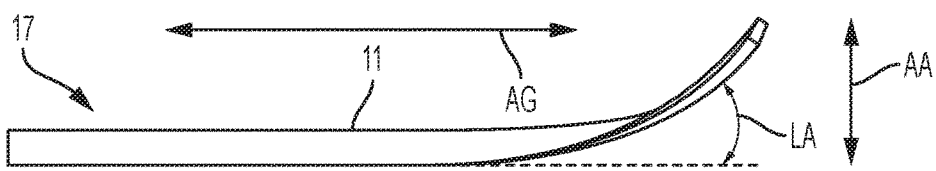
FIG. 5 is a perspective plan view of the elongated member which schematically illustrates the elongated member having been bent in the lateral direction along the lateral axis, AA.

FIG. 5 is a perspective plan view of the elongated member which schematically illustrates the elongated member having been bent laterally, LA, in the lateral direction along the lateral axis, AA, as schematically indicated by angle, LA, along the lateral axis, AA.

Figure 6:
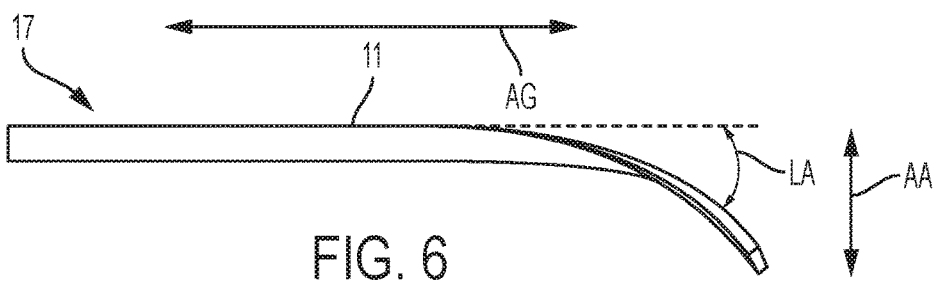
FIG. 6 is a perspective plan view of the elongated member which schematically illustrates the elongated member having been bent in a different lateral direction, compared to FIG. 5, along the lateral axis, AA.

FIG. 6 is a perspective plan view of the elongated member which schematically illustrates the elongated member having been bent laterally, LA, in a different lateral direction (compared to FIG. 5) as schematically indicated by angle, LA, along the lateral axis, AA.

Referring to FIGS. 2-6 the material comprising elongated member 11 may be malleable in this embodiment or in any other embodiment disclosed herein. This malleability may allow for the flexion of the elongated member. This flexion may be accomplished by the user using applying force to different parts of the elongated member 11 or to the retractor device 17 generally, for example using his or her hands to create a bend in the elongated member along the entire longitudinal span, LS, of the elongated member 11. This flexion could also be accomplished via use of a machine to apply such force to create a bend. Along with being bent in the longitudinal direction (as indicated by indicated by angle, LG, for example) as in FIGS. 3 and 4, in the embodiment illustrated in FIGS. 5 and 6 and any other embodiments disclosed herein the elongated member may be capable of being bent or twisted in the lateral direction along the lateral axis, AA (as indicated by indicated by angle, LA, for example). This lateral bend may create a helix or partial helix shape. In these embodiments and any embodiments disclosed herein, the elongated member may be capable of being bent in a first position and may also be capable of being bent into subsequent positions.

The elongated member 11 may have a longitudinal segment that is capable of being configured in a first position and subsequently in a second position. Additionally, the elongated member 11 may be substantially straight or substantially curved in the longitudinal direction along the longitudinal axis, AG. The longitudinal segment of the elongated member 11 may also be substantially straight or substantially curved in the lateral direction along the lateral axis, AA. In another embodiment the elongated member may have a longitudinal segment that may be comprised of multiple segments with one segment being substantially straight or substantially curved. In another embodiment it may be that the elongated member has a longitudinal segment that may be configured into a first position and subsequently in a second position (as well as additional subsequent positions). This first position may be substantially straight while the second position is bent or substantially bent in the longitudinal direction along longitudinal axis, AG, the lateral direction along the lateral axis, AA, or both the longitudinal and lateral directions.

The elongated member 11 may take the shape of a blade, wherein this blade is substantially flat on at least one of its sides. This blade may substantially take the shape of a rectangular prism or substantially rectangular. In other embodiments this blade shape may be approximately a rectangular prism with rounded edges. The elongated member may also have rounded corners. In still other embodiments, one or more of the sides of this elongated member may be curved (concave or convex). Having a curved distal end of the elongated member may help the user to navigate the subject's anatomical region. In other embodiments the blade shape may possess no flat sides.

Figure 7:
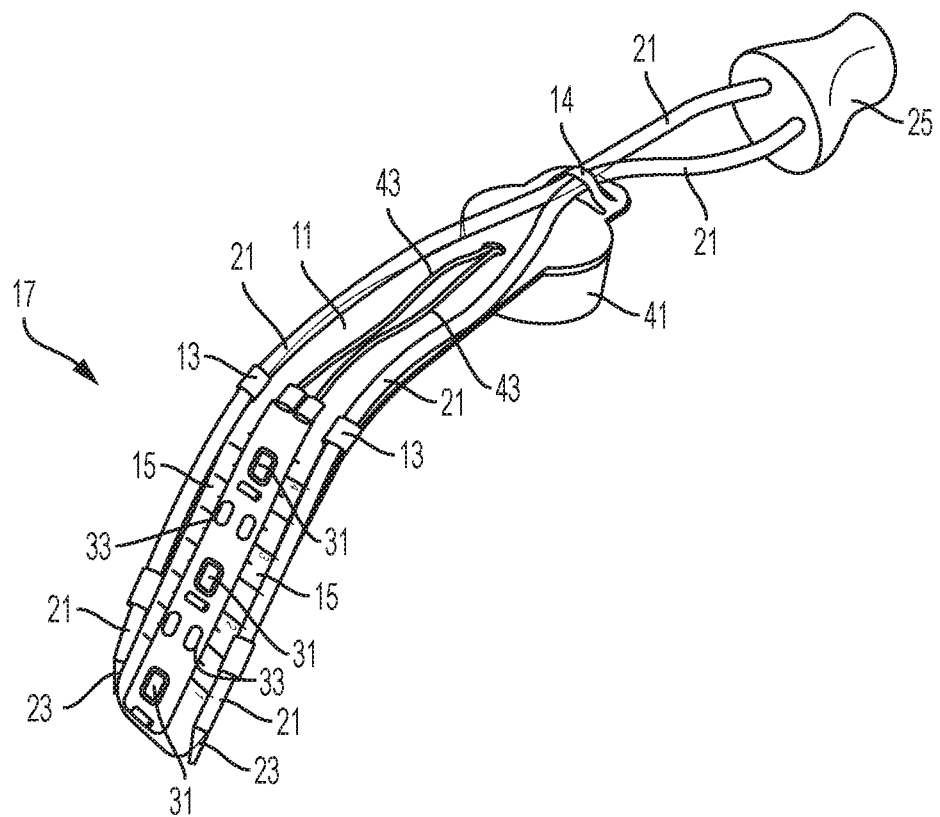
FIG. 7 is a perspective view which schematically illustrates another embodiment of a retractor with lighting and suction capabilities.

FIG. 7 schematically illustrates another exemplary embodiment of the retractor device 17. The suction tubes 21 may be disposed along the entire longitudinal span, LS, of the elongated member 11 (See for example FIGS. 8 and 10) and may be restrained, coupled or attached to the elongated member 11 via one or more retention structures or retainers 13. A retainer may be a clip, clasp, hook, notch, bracket, adhesive material, or the like. In an embodiment, the retainers 13 may be formed of malleable metal or other malleable material which may allow for the opening and closing, loosening, or adjustment of the retainer 13. In an embodiment, the suction tubes 21 may slide, move, or advance within the retainer while the retractor device 17 or elongated member 11 is manipulated. In other embodiments the retainers 13 may be rigid to not allow for opening or loosening by a user but instead hold the suction tubes in their initially designated location.

As mentioned, adhesive material may also be used as retainers to hold the suction tubes in place. Glue, paste, other materials such as hook and loop fasters that are capable of restraining, and the like may be used as adhesive materials. This adhesive material may be permanent to not allow for the adjustment of the suction tubes. In other embodiments this adhesive material may be temporary. This allows for the restraining of the tubes during procedures but allows the user 2 to adjust the tubes as needed during a procedure or between procedures.

These suction tubes 21 may have differently shaped apertures in different embodiments. FIG. 7 illustrates one possible aperture 23 shape with cut for the aperture at a non-perpendicular to the length of the suction tubes. Different aperture shapes may allow for fluid to be withdrawn from the subject without being blocked by tissue or other substances or materials in the anatomical region. In other embodiments, which may possibly be used for procedures where blockage of the aperture is not as high of a concern, the aperture opening may be about or exactly perpendicular to direction of the tube, such as the embodiment illustrated in FIG. 8.

The suction tubes 21 in the embodiment in FIG. 7 may be flexible and capable of being bent by the user in the lateral direction one or more times. The tubes may also be flexible and capable of being bent by the user in the longitudinal direction one or more times. Additionally, these suction tubes 21 may be capable of being bent in the lateral and longitudinal directions one or more times while remaining functional. This bending may twist the suction tubes 21 into a helix or partial helix shape. These capabilities may be in this and other embodiments described herein. These capabilities allow the tubes to continue to provide suction to the desired area of the subject even after the retractor device 17 has been bent in any plane, any number of times.

As with the suction tubes, the light source 31 in this and other embodiments described herein may be disposed along the entire longitudinal span, LS, of the elongated member 11 (See, for example FIGS. 8 and 10) and capable of bending with the elongated member. The light source 31 may be capable of being bent in the lateral direction one or more times. The light source 31 may also be capable of being bent in the longitudinal direction one or more times. Additionally, the light source 31 may be capable of being bent in the lateral and longitudinal directions one or more times while remaining functional all while being located along the entire longitudinal span, LS, of the elongated member 11. This bending may twist the light source 31 into a helix or partial helix shape. These capabilities may be in this and other embodiments described herein. These capabilities allow the light source 31 to continue to provide light emissions 37 (as illustrated in FIGS. 16-20, for example) to the desired area of the subject even after the retractor device 17 has been bent in any plane or series of planes, any number of times. As the user bends said elongated member the light or series of lights may bend with the device, continuing to offer illumination even after the user has deformed the elongated member from a flat planar shape. Therefore, in some embodiments the suction means or suction tubes 21 and light means or light source 31 may both be capable of being configured to coincide with one or more bent positions of the elongated member 11, and wherein the suction tubes 21 and light means or light source 31 may be located along the entire longitudinal span, LS, of the elongated member 11 (See, for example FIGS. 8 and 10). This coinciding may be due to a bending of elongated member 11 and the subsequent movement of the suction tubes 21 and the light source 31 due to their attachment to the elongated member 11. For example, in an embodiment, the suction tubes 21 and the light source 31 may be movably or slidably attached to the elongated member 11 (or to other related components of the retractor device 17).

Referring again to FIG. 7, in this and other embodiments disclosed herein the transmission of power may be accomplished via a single or multiple power transmission lines 43. In this or other embodiments disclosed herein this may be also be accomplished via wireless power transmission. The retractor device 17 may receive this power from a permanent power source, a battery, or from something of the like. This power transmission line 43 in this and other embodiments disclosed herein may be covered in a material which is capable of protecting the transmission line such as an epoxy resign, a polymer, or the like. The covering of this power transmission line may allow the retractor device to be used in a body cavity without fear of harm to the subject or device from fluids which may contact the device.

While some embodiments may use independently powered light sources 31, in other embodiments these light sources may be integrated together. FIG. 7 illustrates circuitry for light sources 33 connecting a series of light sources 31. These circuits may be comprised of wiring of such material as platinum, silver, iron, copper, aluminum, gold, brass, bronze, any similar alloys, or any materials now or to be known in the art to be useful for transmitting power. The light sources in this or other embodiments may be integrated on a chip or other item by a single light source or in a series of light sources. This chip or other item may or may not contain its own built in circuitry for the light source 33. This singular item may then be attached to the elongated member for ease of replacement for situations such as a single light in a combination of light sources is no longer functional.

To assist the user 2 of the retractor device 17 during procedures, in this or any other embodiments disclosed herein, the elongated member 11 may be capable of indicating depth. It may accomplish this by having depth markings 15 on the distal end or any other region of the elongated member. These depth markings may be graduated markings indicating units of length. These markings may be any known way of marking, inscribing, or printing measurements such as etching, printing, writing, carving, or the like. Additionally, in other embodiments these depth markings may be inscribed or marked on a separate item or material which is then attached to the elongated member.

FIG. 7 also illustrates the possible use of a joining mechanism such as a coupling 25, to join the suction tubes 21 if multiple tubes are being used. Additionally, this coupling 25 may be used, instead of for joining together tubes coming from the retractor device 17, to join a suction tube or suction tubes 21 from the retractor device to an auxiliary suction means or suction tube (not shown). This feature may be used alone or in combination with any of the features described herein on this or any other described embodiment.

Figure 9:
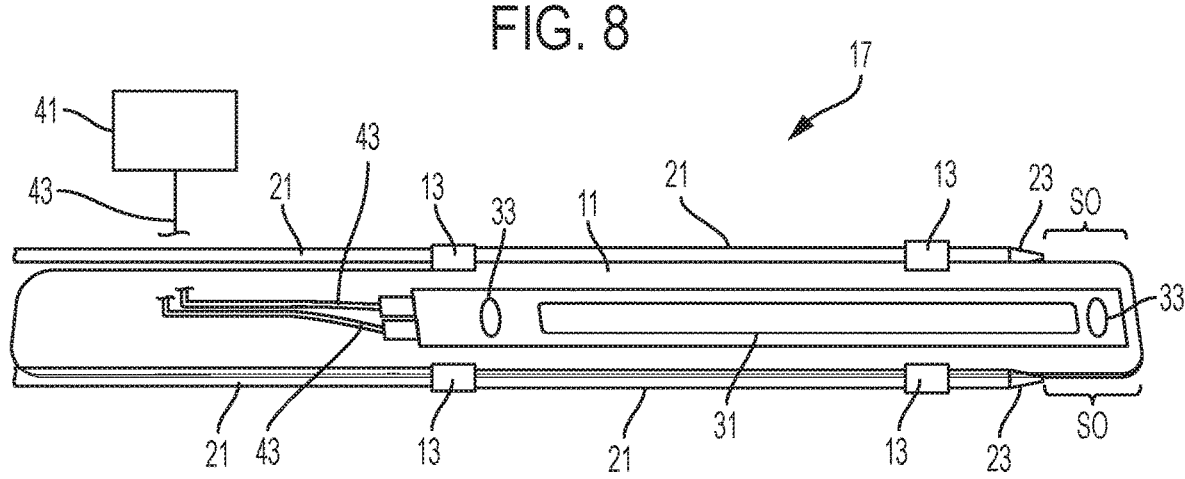
FIG. 9 is another perspective view which schematically illustrates another embodiment of a retractor with lighting and suction capabilities in a flattened or non-bent position.

FIG. 9 is another perspective view which schematically illustrates another embodiment of a retractor device 17 with lighting 31 and suction capabilities 21 in a flattened or non-bent position or shape. FIG. 9 illustrates a retractor device 17 having a singular light source 31. It also illustrates a power supply 41 that is located remotely from the retractor device. These features may be used alone or in combination with any of the features described herein.

Figure 10:
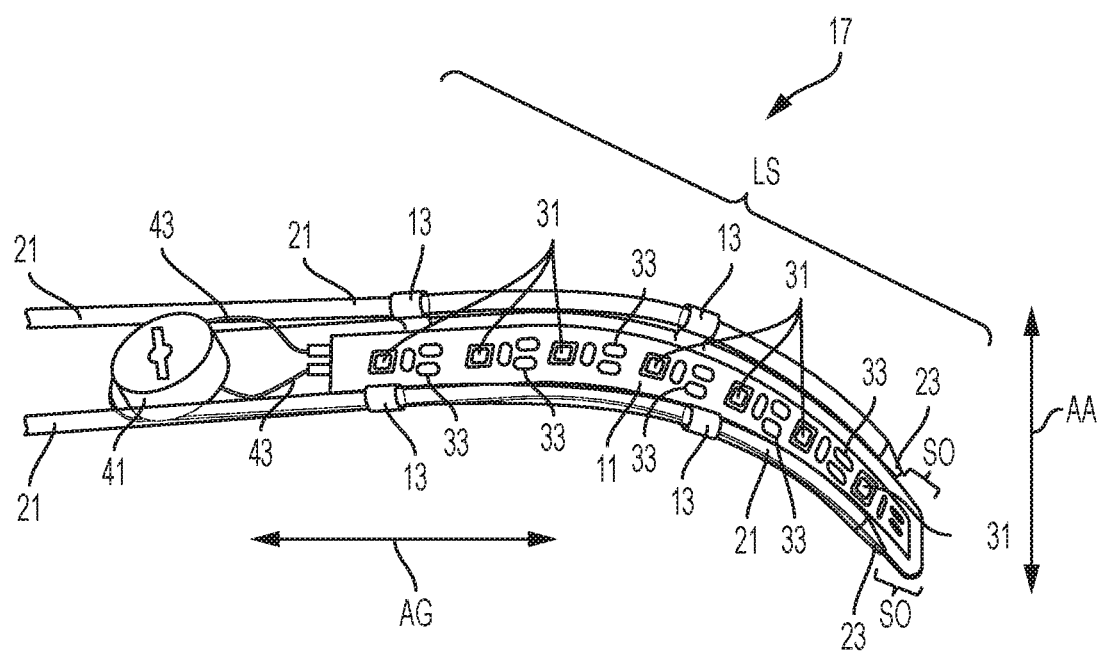
FIG. 10 is a perspective view which schematically illustrates an exemplary embodiment of a retractor with lighting and suction capabilities.

FIG. 10 illustrates an alternative embodiment of a retractor device 17 where the power supply 41 is located locally to the device. Any suitable local power supply can be used, such as a battery. This locally located power supply may be used in this or any other embodiments described herein. This battery may contain a switch to operate the suction means 20 and light source 31 together or multiple switches to operate the suction means and light source independently of each other. FIG. 10 illustrates the suction means 20 and light source 31 may be disposed along the entire longitudinal span, LS, of the elongated member 11. The feature of having a singular switch or the feature of having multiple switches may be implemented on this or any other embodiments described herein, either alone or in combination with any of the other features described in the embodiments herein.

Figure 12:
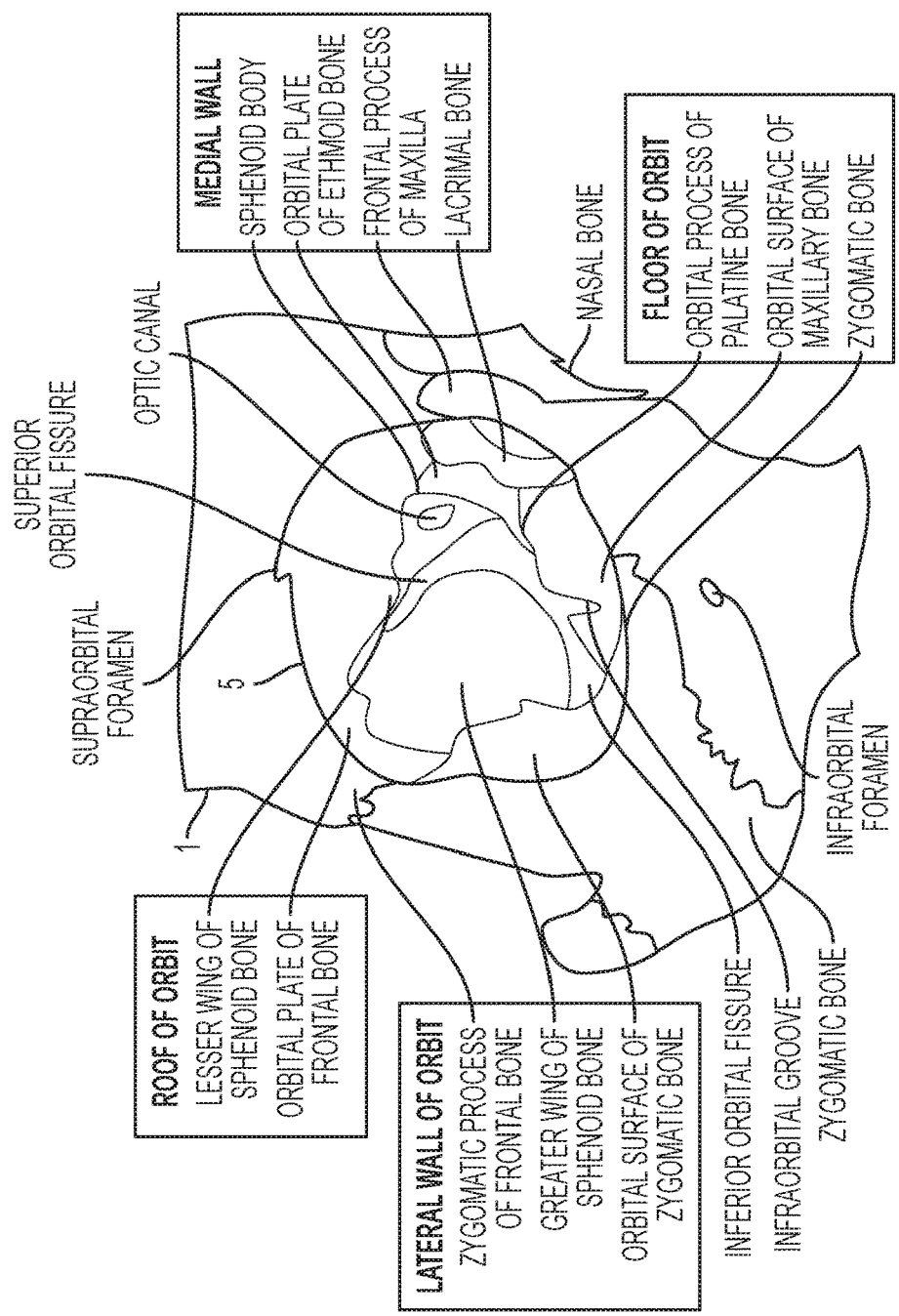
FIG. 12 schematically illustrates the orbital region of a skull as depicted in FIG. 11.
Figure 11:
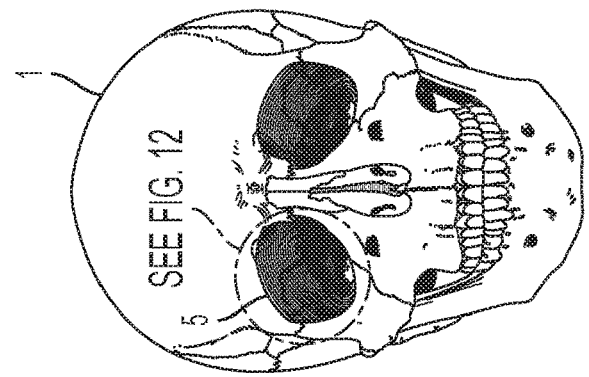
FIG. 11 schematically illustrates the human skull.

FIG. 11 schematically illustrates a subject 1, such as a human skull. FIG. 12 is an enlarged partial view of FIG. 11 schematically illustrating the subject 1 (e.g., the skull) at the orbit 5. Provided is the Roof of the Orbit, which includes: Lesser Wing of Sphenoid Bone and Orbital Plate of Frontal Bone. Provided is the Lateral Wall of the Orbit, which includes: Zygomatic Process of Frontal Bone, Greater Wing of Sphenoid Bone, and Orbital Surface of Zygomatic Bone. Provided is the Floor of the Orbit, which includes: Orbital Process of Palatine Bone, Orbital Surface of Maxillary Bone, and Zygomatic Bone. Provided is the Medial Wall, which includes: Sphenoid Body, Orbital Plate of Ethmoid Bone, Frontal Process of Maxilla, and Lacrimal Bone. Also provided is the Supraorbital Foramen, Superior Orbital Fissure, Optic Canal, Nasal Bone, Infraorbital Foramen, Zygomatic Bone, Infraorbital Groove, and Inferior Orbital Fissure.

Figure 13:
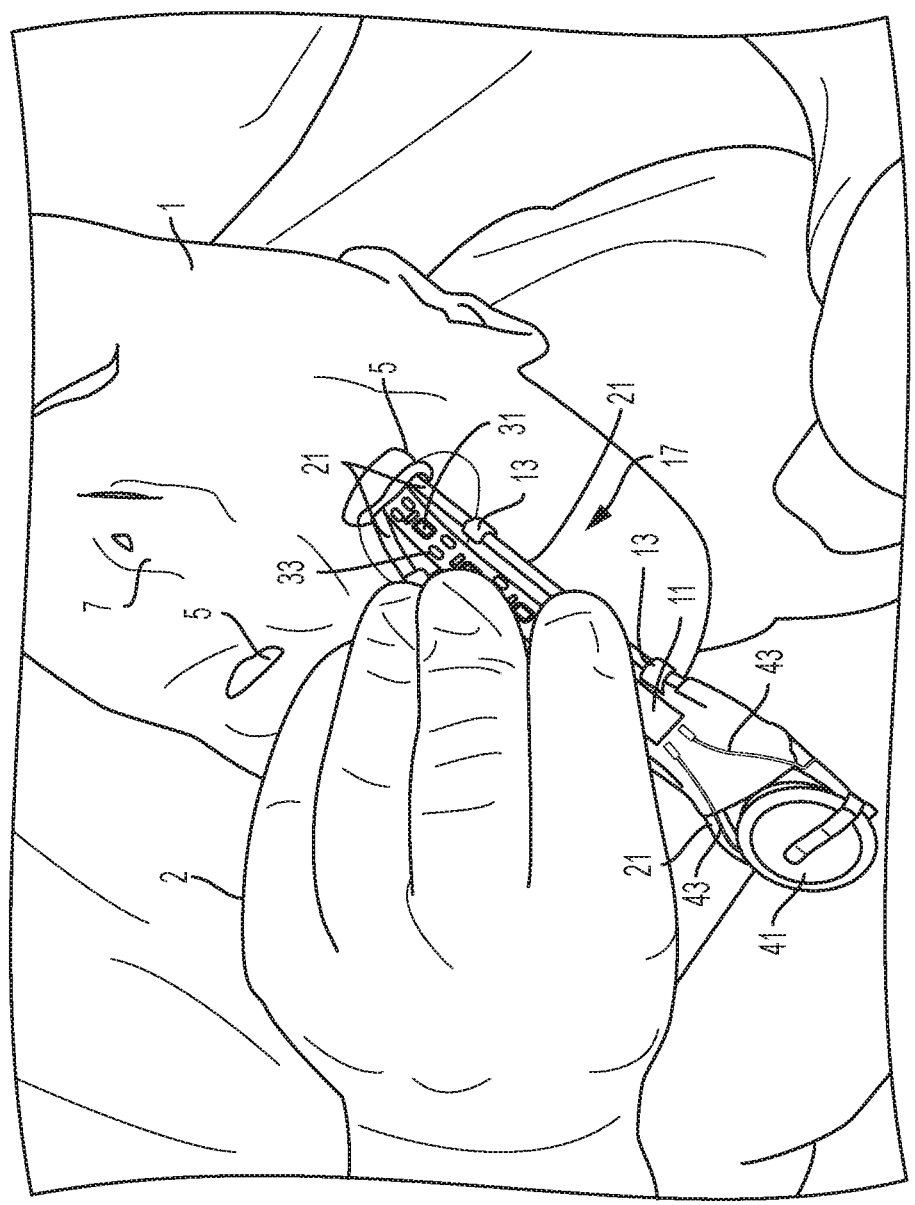
FIG. 13 schematically illustrates a user using the retractor device on a subject's orbital cavity.

FIG. 13 schematically illustrates a user 2 using the retractor device 17 on a subject's orbital cavity 5. This, along with FIG. 14, schematically illustrates the possibility of the retractor device 17 being used to gain access to an anatomical region of a subject 1, wherein this access may include the drawing back of a subject's bone or tissue; as well as manipulating other tissue, implants or material.

FIG. 14 schematically illustrates how a user (not shown) may use the retractor device 17 in conjunction with the insertion of reconstructive material or implants in a subject's orbital cavity 5. FIG. 14 also schematically illustrates how the retractor device 17 may be used for the elevation or retraction of the tissue or eye 6 of a subject 1.

FIGS. 13-14 illustrate other exemplary embodiments of an illuminated suction retractor device 17 being used in various exemplary procedures on the orbital region of a subject 1. The elongated member 11, as previously mentioned, may be formed out of malleable material. The malleable nature of the retractor device 17 in these embodiments allows for the surgeon or user 2 to bend the device 17 to fit into the anatomical region (e.g., orbit 5) of the subject 1. This bent device is then better able to enter the orbit 5 region and retract tissue near the eye 6. The materials for the elongated member 11 are anything metal or nonmetal that can bend with pressure from the hand of the user 2 but retain its position against tissue during use. As illustrated by an embodiment in FIG. 14 the retractor device 17 may not substantially deform or may not deform at all when used to apply pressure and retract the tissue surrounding the eye 6 during the insertion of an implant 8. This allows a user 2 or surgeon to shape the elongated member 11 or retractor device 17 to exactly the shape he requires but continue to have the retractor device 17 maintain this shape during use. The users may bend and shape the elongated member 11 numerous times throughout the course of the surgery to meet the various intended shapes of the elongated member respective to gaining access to the various areas of the anatomical region, such as the eye 6 or orbit 5 (as well as for placement of implants 8, 9 and other material).

The elongated member 11, as previously mentioned, may be formed out of malleable material. Accordingly, the elongated member 11 and related components of the retractor device 17 may be bent or positioned in a suitable manner. Accordingly, the elongated member 11 and related components of the retractor device 17 are configured to hold their shape once arranged in a desired position by the user or surgeon. Accordingly, the elongated member 11 and related components of the retractor device 17 may have a "memory" such as SMA and thus will not return back to the original shape after deformation by the user or surgeon. The "memory" or SMA can hold a shape once bent but then with a stimulus may return to a pre-deformed shape or position. Accordingly, the elongated member 11 and related components of the retractor device 17 may retain their desired bent or shaped positons until manipulated into another shape or contour.

The elongated member 11 or related components of the retractor device 17 may possess a modulus of elasticity or Young's modulus in the range of about 60 GPa to about 250 GPa.

The elongated member 11 or related components of the retractor device 17 may possess a modulus of elasticity or Young's modulus in the range of about 190 GPa to about 205 GPa.

The elongated member 11 or related components of the retractor device 17 may possess a modulus of elasticity or Young's modulus of about 193 GPa.

The elongated member 11 or related components of the retractor device 17 may possess a modulus of elasticity or Young's modulus in the range of about 80 GPa to about 230 GPa.

The elongated member 11 or related components of the retractor device 17 may possess a modulus of elasticity or Young's modulus in the range of about 100 GPa to about 210 GPa.

The elongated member 11 or related components of the retractor device 17 may possess a modulus of elasticity or Young's modulus in the range of about 120 GPa to about 190 GPa.

The elongated member 11 or related components of the retractor device 17 may possess a modulus of elasticity or Young's modulus in the range of about 140 GPa to about 170 GPa.

The elongated member 11 or related components of the retractor device 17 may possess a modulus of elasticity or Young's modulus in the range of about 140 GPa to about 250 GPa.

The elongated member 11 or related components of the retractor device 17 may possess a modulus of elasticity or Young's modulus in the range of about 60 GPa to about 170 GPa.

In an embodiment, the aforementioned exemplary, and non-limiting, list of modulus of elasticity or Young's modulus may be greater than or less than as desired for applied anatomical requirements or surgical procedures.

The elongated member 11 or related components of the retractor device 17 may possess a flexural modulus or bend modulus in the range of about 60 GPa to about 250 GPa.

The elongated member 11 or related components of the retractor device 17 may possess a flexural modulus or bend modulus in the range of about 190 GPa to about 205 GPa.

The elongated member 11 or related components of the retractor device 17 may possess a flexural modulus or bend modulus of about 193 GPa.

The elongated member 11 or related components of the retractor device 17 may possess a flexural modulus or bend modulus in the range of about 80 GPa to about 230 GPa.

The elongated member 11 or related components of the retractor device 17 may possess a flexural modulus or bend modulus in the range of about 100 GPa to about 210 GPa.

The elongated member 11 or related components of the retractor device 17 may possess a flexural modulus or bend modulus in the range of about 120 GPa to about 190 GPa.

The elongated member 11 or related components of the retractor device 17 may possess a flexural modulus or bend modulus in the range of about 140 GPa to about 170 GPa.

The elongated member 11 or related components of the retractor device 17 may possess a flexural modulus or bend modulus in the range of about 140 GPa to about 250 GPa.

The elongated member 11 or related components of the retractor device 17 may possess a flexural modulus or bend modulus in the range of about 60 GPa to about 170 GPa.

In an embodiment, the aforementioned exemplary, and non-limiting, list of flexural modulus or bend modulus may be greater than or less than as desired for applied anatomical requirements or surgical procedures.

As this embodiment is able to provide retraction while also providing suction means 20 and a light source 31, this may allow a user 2 to operate an ancillary tool or instrument 10 to assist in the procedure. In these or in any other embodiments described herein, when this device is being used for this or other procedures it may be used in conjunction with another implant 8 as desired or required, an orbital floor implant 9, or the delivery of synthetic material which may be utilized to reinforce the orbital floor.

Figure 15:
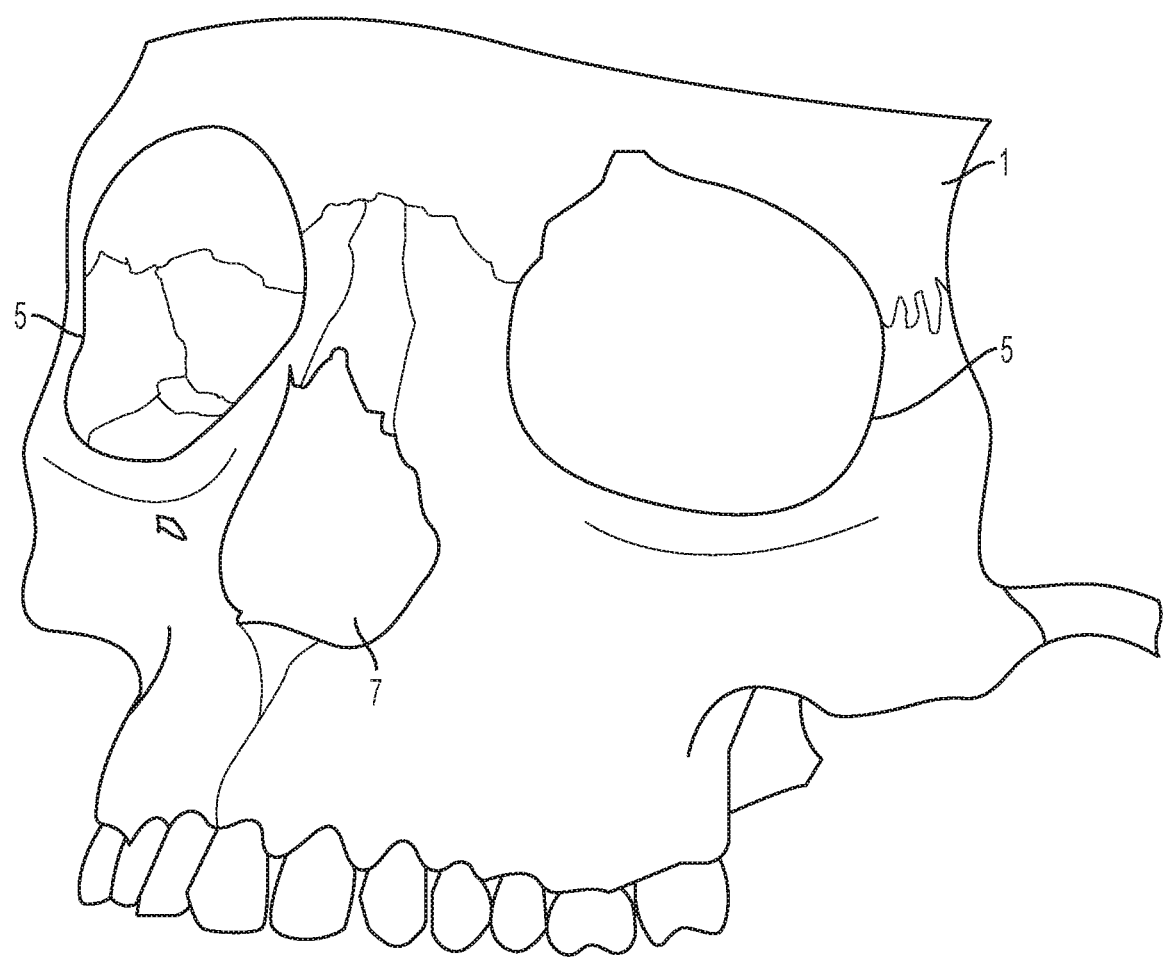
FIG. 15 schematically illustrates an exemplary region of a subject's skull.

FIG. 15 schematically illustrates an exemplary region of a subject 1 such as a subject's skull, and orbit 5 and nasal cavity 7.

Figure 16:
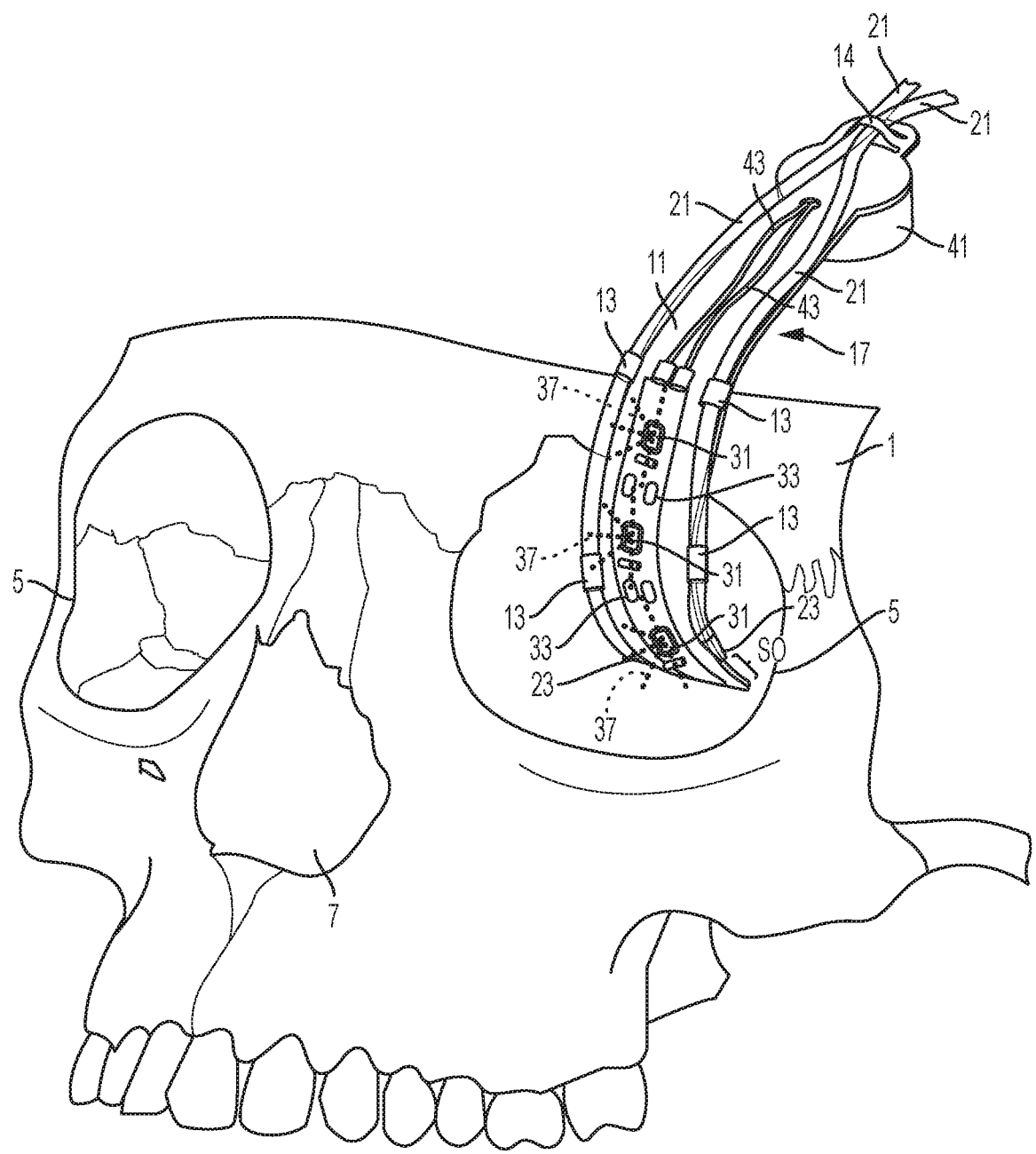
FIG. 16 schematically illustrates an exemplary retractor device being inserted into a subject's skull in a bent position.

FIG. 16 illustrates another embodiment of the retractor device 17. This embodiment utilizes an upper retainer 14 that may be on or adjacent to the proximal end (or other component) of the elongated member 11 to hold the tubes in proximity to each other and close to the proximal end of the elongated member. This retainer 14 may be a band, opening, clip, slip, or any retainer of the like. This feature may be used whether there is only a single suction tube 21 or multiple suction tubes 21. This may be accomplished via an opening as illustrated in FIG. 16 or via any suitable retaining means such as that similarly described for the retainers 13. This feature may be used alone or in combination with any of the features described in any of the embodiments disclosed herein.

FIG. 16 additionally illustrates the malleable nature of this embodiment and a feature which may be part of other embodiments described herein. This feature allows the retractor device 17 to be bent by a user to fit properly into the orbit 5 of a subject 1.

Figure 17:
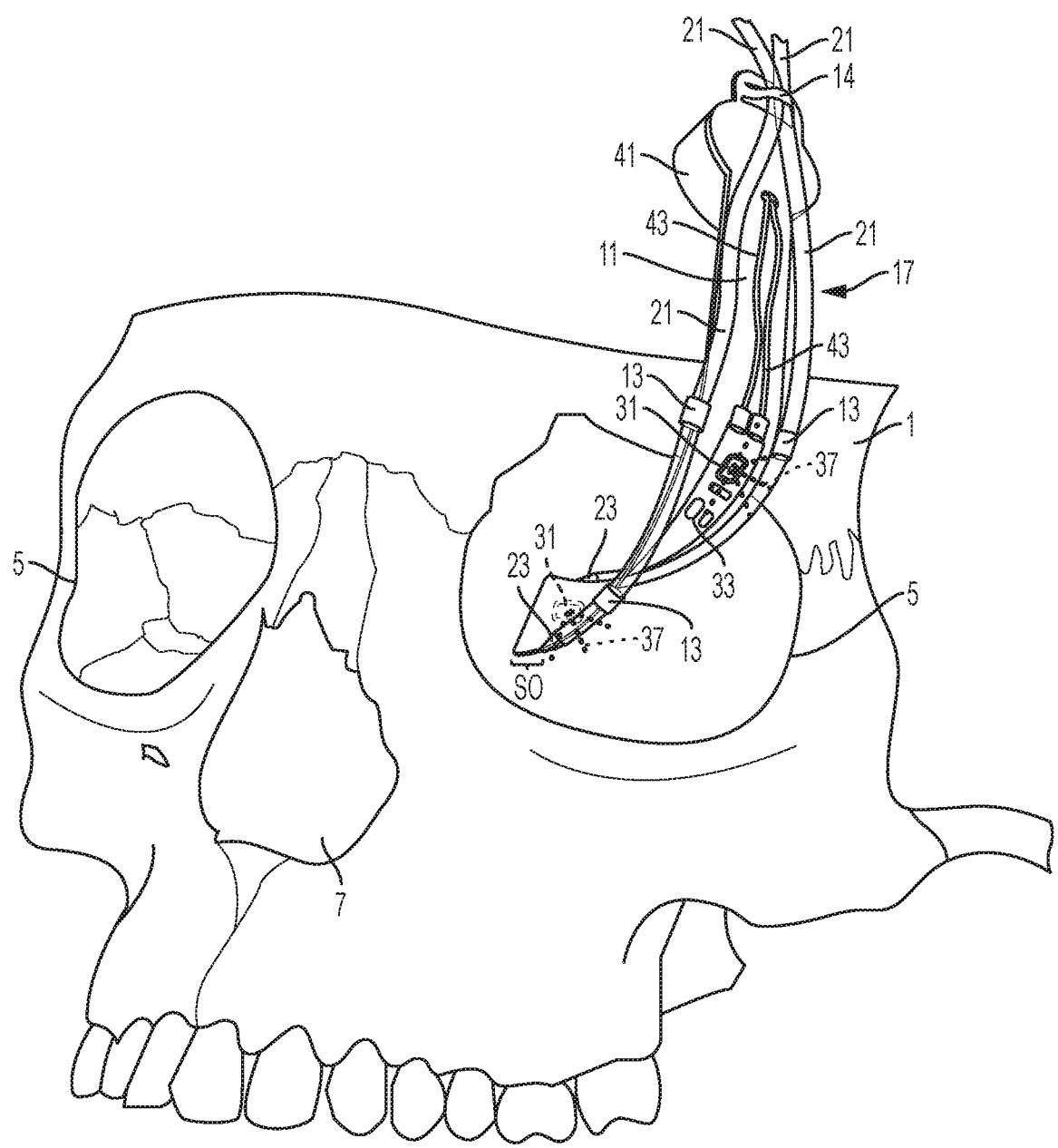
FIG. 17 schematically illustrates an exemplary retractor device being inserted into a subject's skull in a subsequent bent position.

FIG. 17 illustrates an embodiment of the retractor device 17 after it has been bent in multiple planes, along the longitudinal axis and also along the lateral axis. This bending has twisted the retractor device 17 into a partial helix shape. While the suction tubes 21 and the light source 31 have been bent with the retractor device 17, both the suction tubes 21 and the light source 31 remain operational. This light source 31 has an emission of light 37 projecting from it to illuminate the anatomical region of the subject 1. This light emission 37 may project in all directions outwardly or may be directed to provide pinpoint illumination. The feature of the suction tubes and the light source being capable of being bent and continuing to remain functional may be incorporated, by itself or in combination with any other feature described, into any other embodiment described herein. In this illustrated embodiment (FIG. 17), the light sources 31 are on the same side of the elongated member 11.

Figure 19:
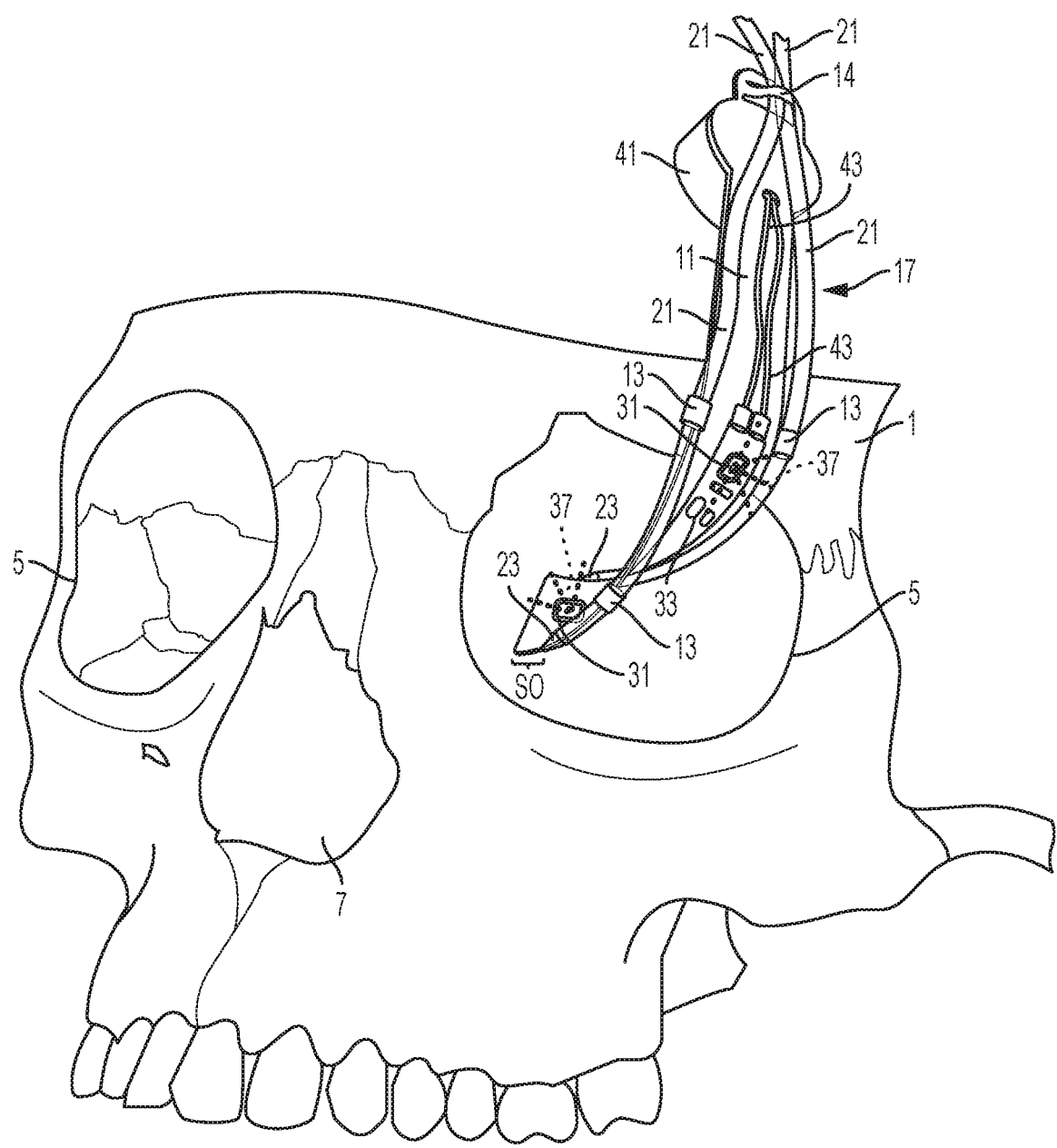
FIG. 19 schematically illustrates an exemplary retractor device with light sources on multiple sides being inserted into a subject's skull in a subsequent bent position.

Referring now to FIG. 19, this embodiment also shows how, similarly to the embodiment in FIG. 17, the retractor device may be bent in multiple planes but the light source and suction tubes remain functional. The difference in this embodiment though is that the light source 31 may include light sources on multiple sides of the elongated member 11. This light source 31 has an emission of light 37 projecting from it to illuminate the anatomical region of the subject 1. This light emission 37 may project in all directions outwardly or may be directed to provide pinpoint illumination. As in this embodiment there are light sources 31 on multiple sides of the elongated member 11, this may offer greater illumination of the subject's anatomical region. The light sources 31 may be disposed along the entire longitudinal span, LS, of the elongated member 11. This may be the case on this or any of the other embodiments described herein.

Figure 18:
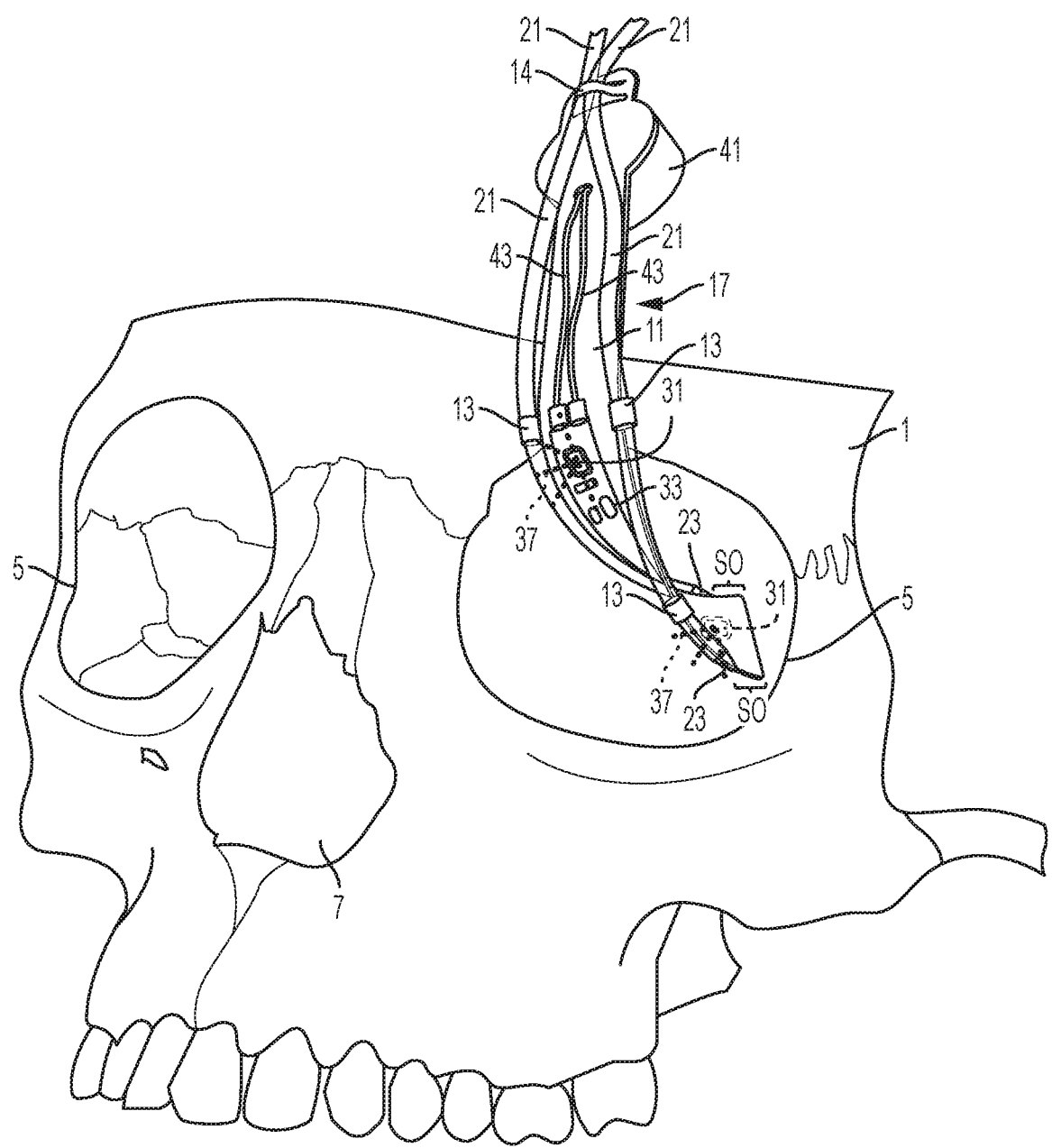
FIG. 18 schematically illustrates an exemplary retractor device being inserted into a subject's skull in a subsequent bent position.

FIGS. 17-18 illustrate how an embodiment of the retractor device 17 is capable of being bent to sweep in the opposite lateral directions, transitioning from a position similar to that shown in FIG. 17 to a position similar to that shown in FIG. 18. Whereas, for example, the retractor device 17 illustrated in FIG. 16 is shown having been bent downward in a longitudinal direction. Although not illustrated in FIG. 16, the retractor device 17 may also be bent upward by the user in a longitudinal direction. Although not illustrated in FIG. 16, the retractor device 17 may also be bent by the user in any combination of various longitudinal directions and lateral directions and achieve helical or semi-helical shapes (e.g., various twist or curved shapes and contours).

FIG. 18 illustrates an embodiment of the retractor device 17 after it has been bent in multiple planes, along the longitudinal axis and also along the lateral axis. This bending has twisted the retractor device 17 into a partial helix shape. While the suction tubes 21 and the light source 31 have been bent with the retractor device 17, both the suction tubes 21 and the light source 31 remain operational. The feature of the suction tubes and the light source being capable of being bent and continuing to remain functional may be incorporated, by itself or in combination with any other feature described, into any other embodiment described herein. In this illustrated embodiment (FIG. 18), the light sources 31 are on the same side of the elongated member 11.

Figure 20:
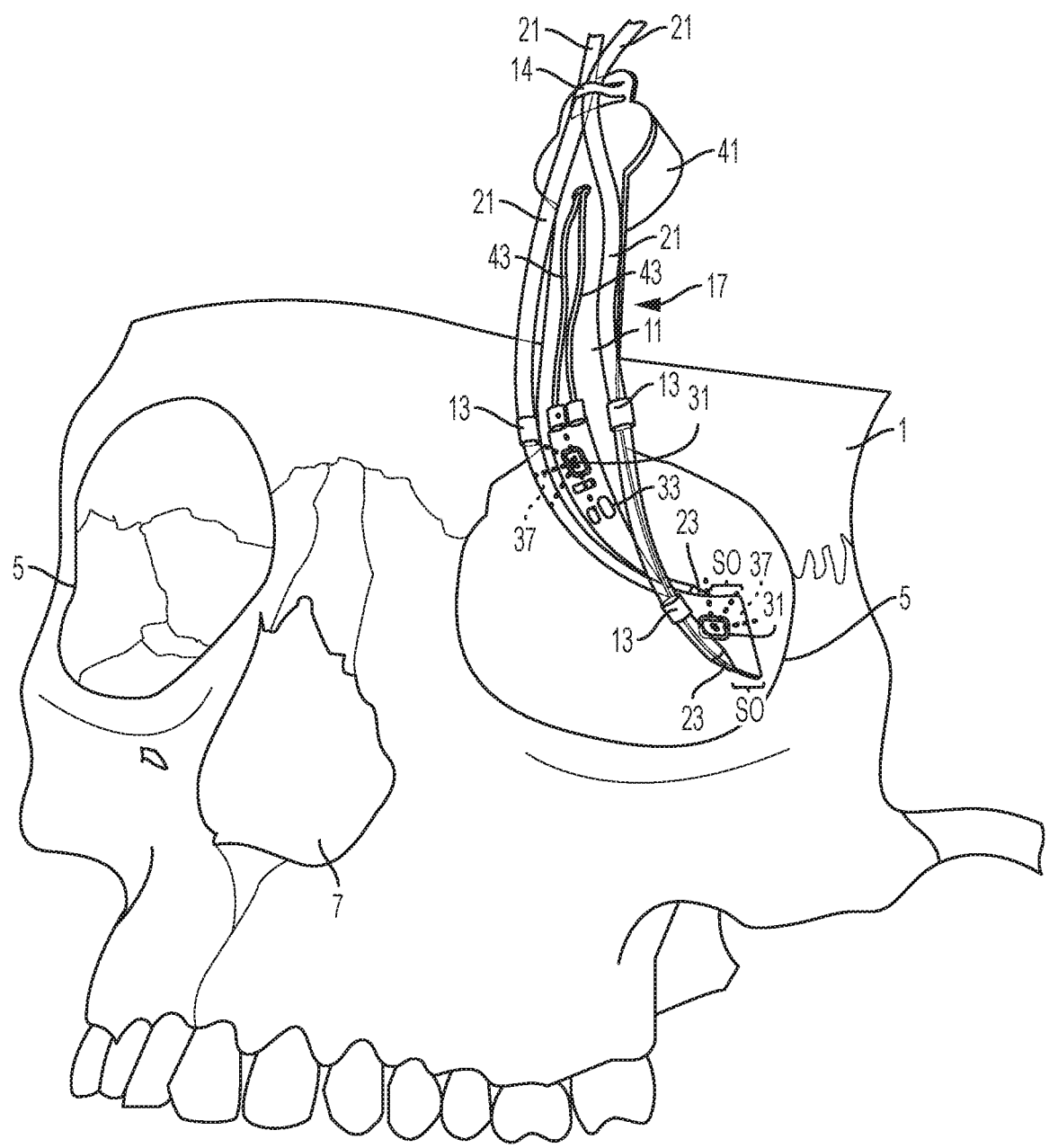
FIG. 20 schematically illustrates an exemplary retractor device with light sources on multiple sides being inserted into a subject's skull in a subsequent bent position.

Referring now to FIG. 20, this embodiment also shows how similarly to the embodiment in FIG. 18, the retractor device may be bent in multiple planes but the light source and suction tubes remain functional. This bending has twisted the retractor device 17 into a partial helix shape. The difference in this embodiment though is that the light source 31 may include light sources on both sides of the elongated member 11. This may be the case on this or any of the other embodiments described herein.

FIGS. 19-20 illustrate how an embodiment of the retractor device 17 is capable of being bent to sweep in the opposite lateral directions, transitioning from a position similar to that shown in FIG. 19 to a position similar to that shown in FIG. 20. This bending has twisted the retractor device 17 into a partial helix shape. In this and other embodiments the retractor device 17 may be bent multiple times to change the sweep and direction of the bend or curve of the retractor device 17.

EXAMPLES

Practice of an aspect of an embodiment (or embodiments) of the invention will be still more fully understood from the following examples and experimental results, which are presented herein for illustration only and should not be construed as limiting the invention in any way.

Example 1

A retractor device for accessing an anatomical region of a subject. The device may comprise: an elongated member having a distal end and a proximal end with a longitudinal segment extending there between, wherein said distal end of said elongated member is configured to access the anatomical region; one or more tubes capable of providing suction, said one or more tubes disposed on said elongated member and said one or more tubes include a distal aperture, wherein distal apertures of said tubes are located at or proximate to the distal end of said elongated member, and said distal apertures are configured to provide the suction to the anatomical region; one or more light sources coupled to said elongated member, said light sources capable of providing light, and said light sources configured to provide lighting to the anatomical region; and said longitudinal member of said elongated member is configured to be bent in one or more positions in response to manual forces that may be applied by a user onto said elongated member, and wherein said tubes remain operable to provide suction in said one or more bent positions and said light sources remain operable to provide light in said one or more bent positions.

Example 2

The device of example 1, wherein said device is configured to communicate with a power supply.

Example 3

The device of example 2, wherein said power supply is located locally to said device.

Example 4

The device of example 2 (as well as subject matter in whole or in part of example 3), wherein said power supply is located remotely from said device.

Example 5

The device of example 1 (as well as subject matter of one or more of any combination of examples 2-4, in whole or in part), wherein said elongated member is a blade.

Example 6

The device of example 5, wherein said blade is flat on two of its sides.

Example 7

The device of example 5 (as well as subject matter in whole or in part of example 6), wherein said blade is concave or convex on two of its sides in the lateral direction.

Example 8

The device of example 1 (as well as subject matter of one or more of any combination of examples 2-7, in whole or in part), wherein said elongated member is comprised of malleable material possessing a modulus of elasticity or Young's modulus in the range of about 60 GPa to about 250 GPa.

Example 9

The device of example 1 (as well as subject matter of one or more of any combination of examples 2-8, in whole or in part), wherein said elongated member is comprised of malleable material possessing a modulus of elasticity or Young's modulus in the range of about 190 GPa to about 205 GPa.

Example 10

The device of example 1 (as well as subject matter of one or more of any combination of examples 2-9, in whole or in part), wherein said elongated member is comprised of malleable material possessing a modulus of elasticity or Young's modulus of about 193 GPa.

Example 11

The device of example 1 (as well as subject matter of one or more of any combination of examples 2-10, in whole or in part), wherein said elongated member is comprised of malleable material possessing a flexural modulus or bend modulus in the range of about 60 GPa to about 250 GPa.

Example 12

The device of example 1 (as well as subject matter of one or more of any combination of examples 2-11, in whole or in part), wherein said elongated member is comprised of malleable material possessing a flexural modulus or bend modulus in the range of about 190 GPa to about 205 GPa.

Example 13

The device of example 1 (as well as subject matter of one or more of any combination of examples 2-12, in whole or in part), wherein said elongated member is comprised of malleable material possessing a flexural modulus or bend modulus of about 193 GPa.

Example 14

The device of example 1 (as well as subject matter of one or more of any combination of examples 2-13, in whole or in part), wherein said elongated member is comprised of malleable material possessing a flexural modulus or bend modulus in the range of one of the following ranges:
- about 80 GPa to about 230 GPa;
- about 100 GPa to about 210 GPa;
- about 120 GPa to about 190 GPa;
- about 140 GPa to about 170 GPa;
- about 140 GPa to about 250 GPa; or
- about 60 GPa to about 170 GPa.

Example 15

The device of example 1 (as well as subject matter of one or more of any combination of examples 2-14, in whole or in part), wherein said elongated member is comprised of malleable material where said malleable material is defined as being capable of being bent in said one or more positions in response to the manual forces by the user but not substantially bending in response to forces incurred from said elongated member accessing the anatomical region.

Example 16

The device of example 15, wherein said one or more tubes and said one or more light sources is configured to coincide with said one or more bent positions of said elongated member.

Example 17

The device of example 1 (as well as subject matter of one or more of any combination of examples 2-16, in whole or in part), wherein said elongated member is capable of being bent in the longitudinal direction.

Example 18

The device of example 17, wherein said tubes and/or said light sources are capable of being bent in the longitudinal direction.

Example 19

The device of example 1 (as well as subject matter of one or more of any combination of examples 2-18, in whole or in part), wherein said elongated member is capable of being bent a plurality of occurrences in the longitudinal direction.

Example 20

The device of example 19, wherein said tubes and/or said light sources are capable of being bent a plurality of occurrences in the longitudinal direction.

Example 21

The device of example 1 (as well as subject matter of one or more of any combination of examples 2-20, in whole or in part), wherein said elongated member is capable of being bent in the lateral direction.

Example 22

The device of example 21, wherein said tubes and/or said light sources are capable of being bent in the lateral direction.

Example 23

The device of example 1 (as well as subject matter of one or more of any combination of examples 2-22, in whole or in part), wherein said elongated member is capable of being bent a plurality of occurrences in the lateral direction.

Example 24

The device of example 23, wherein said tubes and/or said light sources are capable of being bent a plurality of occurrences in the lateral direction.

Example 25

The device of example 1 (as well as subject matter of one or more of any combination of examples 2-24, in whole or in part), wherein said elongated member is capable of being bent in both a longitudinal direction and lateral direction.

Example 26

The device of example 25, wherein said tubes and/or said light sources are capable of being bent in both a longitudinal direction and lateral direction.

Example 27

The device of example 25 (as well as subject matter of one or more of any combination of examples 2-24, in whole or in part), wherein said bent longitudinal and lateral directions of said elongated member provides for said elongated member being in a helix shape or partial helix shape.

Example 28

The device of example 27 (as well as subject matter of one or more of any combination of examples 2-26, in whole or in part), wherein said bent longitudinal and lateral directions of said tubes and/or said light sources provides for said tubes and/or said light sources being in a helix shape or partial helix shape.

Example 29

The device of example 1 (as well as subject matter of one or more of any combination of examples 2-28, in whole or in part), wherein said elongated member is capable of being bent a plurality of occurrences in both a longitudinal direction and lateral direction.

Example 30

The device of example 29, wherein said tubes and/or said light sources are capable of being bent a plurality of occurrences in both a longitudinal direction and lateral direction.

Example 31

The device of example 29 (as well as subject matter of one or more of any combination of examples 2-28, in whole or in part), wherein said bent longitudinal and lateral directions of said elongated member provides for said elongated member being in a helix shape or partial helix shape.

Example 32

The device of example 31, wherein said bent longitudinal and lateral directions of said tubes and/or said light sources provides for said tubes and/or said light sources being in a helix shape or partial helix shape.

Example 33

The device of example 1 (as well as subject matter of one or more of any combination of examples 2-32, in whole or in part), wherein the distal end of said elongated member is capable of indicating depth.

Example 34

The device of example 1 (as well as subject matter of one or more of any combination of examples 2-33, in whole or in part), wherein said elongated member further comprises graduated markings indicating units of length.

Example 35

The device of example 1 (as well as subject matter of one or more of any combination of examples 2-34, in whole or in part), wherein said elongated member includes a top portion and a bottom portion, and wherein said light sources are coupled to said top portion of said elongated member.

Example 36

The device of example 1 (as well as subject matter of one or more of any combination of examples 2-35, in whole or in part), wherein said elongated member includes a top portion and a bottom portion, and wherein said light sources are coupled to said bottom portion of said elongated member.

Example 37

The device of example 1 (as well as subject matter of one or more of any combination of examples 2-36, in whole or in part), wherein said elongated member includes a top portion and a bottom portion, and wherein said device comprises a plurality of light sources, wherein said light sources are respectively coupled on both said bottom portion and said top portion of said elongated member.

Example 38

The device of example 1 (as well as subject matter of one or more of any combination of examples 2-37, in whole or in part), wherein said elongated member includes a top portion and a bottom portion, and wherein said tubes are coupled to said top portion of said elongated member.

Example 39

The device of example 1 (as well as subject matter of one or more of any combination of examples 2-38, in whole or in part), wherein said elongated member includes a top portion and a bottom portion, and wherein said tubes are coupled to said bottom portion of said elongated member.

Example 40

The device of example 1 (as well as subject matter of one or more of any combination of examples 2-39, in whole or in part), wherein said elongated member includes a top portion and a bottom portion, and wherein said tubes are respectively coupled on both said bottom portion and said top portion of the elongated member.

Example 41

The device of example 1 (as well as subject matter of one or more of any combination of examples 2-40, in whole or in part), wherein said tubes are substantially oppositely opposed on said elongated member.

Example 42

The device of example 1 (as well as subject matter of one or more of any combination of examples 2-41, in whole or in part), wherein said tubes are coupled to substantially oppositely opposed sides of said elongated member.

Example 43

The device of example 1 (as well as subject matter of one or more of any combination of examples 2-42, in whole or in part), wherein said elongated member includes a retention material or one or more retention structures for retaining said one or more tubes.

Example 44

The device of example 43, wherein said retention structure movably retains said one or more tubes.

Example 45

The device of example 43 (as well as subject matter of one or more of any combination of examples 2-42 and 44, in whole or in part), wherein said retention structure includes at least one or more of any combination of the following: clip, clasp, hook, notch, and bracket.

Example 46

The device of example 43 (as well as subject matter of one or more of any combination of examples 2-42 and 44-45, in whole or in part), wherein said retention material comprises an adhesive material.

Example 47

The device of example 1 (as well as subject matter of one or more of any combination of examples 2-46, in whole or in part), wherein said longitudinal segment of said elongated member is substantially straight in the longitudinal direction.

Example 48

The device of example 1 (as well as subject matter of one or more of any combination of examples 2-47, in whole or in part), wherein said longitudinal segment of said elongated member is curved in the longitudinal direction.

Example 49

The device of example 1 (as well as subject matter of one or more of any combination of examples 2-48, in whole or in part), wherein said longitudinal segment of said elongated member is curved in the lateral direction.

Example 50

The device of example 1 (as well as subject matter of one or more of any combination of examples 2-49, in whole or in part), wherein said longitudinal segment of said elongated member is curved in both the longitudinal direction and lateral direction.

Example 51

The device of example 1 (as well as subject matter of one or more of any combination of examples 2-50, in whole or in part), wherein said longitudinal segment of said elongated member is comprised of multiple segments with one portion of said elongated member being substantially curved.

Example 52

The device of example 1 (as well as subject matter of one or more of any combination of examples 2-51, in whole or in part), wherein said longitudinal segment of said elongated member is capable of being configured in a first position and subsequently in a second position.

Example 53

The device of example 52, wherein said first position is substantially straight in the longitudinal direction and said second position is bent or substantially bent in either the:
  longitudinal direction,
  lateral direction, or
  both said longitudinal and lateral direction.

Example 54

The device of example 1 (as well as subject matter of one or more of any combination of examples 2-53, in whole or in part), wherein the access of the anatomical region includes drawing back of a subject's bone or tissue.

Example 55

The device of example 1 (as well as subject matter of one or more of any combination of examples 2-54, in whole or in part), wherein said elongated member is capable of elevating tissue of the anatomical region.

Example 56

The device of example 1 (as well as subject matter of one or more of any combination of examples 2-55, in whole or in part), wherein said elongated member is capable of retracting tissue of the anatomical region.

Example 57

The device of example 1 (as well as subject matter of one or more of any combination of examples 2-56, in whole or in part), wherein the elongated member is comprised of one or more of the following materials: steel, 301 stainless steel, stainless steel, titanium, copper, nickel, rubber, shape-memory alloy (SMA), injection moldable plastic, or plastic.

Example 58

The device of example 1 (as well as subject matter of one or more of any combination of examples 2-57, in whole or in part), wherein said light source includes at least one of the following: LED or fiber optic.

Example 59

The device of example 1 (as well as subject matter of one or more of any combination of examples 2-58, in whole or in part), further comprising a kit which comprises any one or more of the following: one or more plates for placement in the anatomical region, one or more screws, a retractor, a scalpel, a device for delivery of synthetic material, a device for delivery of an implant, or a cautery tool.

Example 60

A device for accessing an anatomical region of a subject. The device may comprise: a retraction means for accessing the anatomical region of a subject, wherein said retraction means is configured to be bent in one or more positions in response to forces that may be applied by a user onto the retraction means; a suction means for providing suction to the anatomical region; a lighting means for providing light to the anatomical region; and wherein said retraction means, suction means, and lighting means are capable of being provided simultaneously while said retraction means is bent in the one or more positions.

Example 61

The device of example 60, wherein said suction means and said lighting means are configured to coincide with said one or more bent positions of said retraction means.

Example 62

The device of example 60 (as well as subject matter in whole or in part of example 61), wherein said suction means is configured to be bent in said one or more bent positions.

Example 63

The device of example 60 (as well as subject matter of one or more of any combination of examples 61-62, in whole or in part), wherein said lighting means is configured to be bent in said one or more bent positions.

Example 64

The device of example 60 (as well as subject matter of one or more of any combination of examples 61-63, in whole or in part), wherein said suction means and said lighting means are configured to be bent in said one or more bent positions.

Example 65

The device of example 60 (as well as subject matter of one or more of any combination of examples 61-64, in whole or in part), wherein said retraction means possesses a modulus of elasticity or Young's modulus in the range of about 60 GPa to about 250 GPa.

Example 66

The device of example 60 (as well as subject matter of one or more of any combination of examples 61-65, in whole or in part), wherein said retraction means is capable of being bent in said one or more positions in response to the manual forces by the user but not substantially bending in response to forces incurred from said retraction means accessing the anatomical region.

Example 67

The method of manufacturing any of the devices (or their components and subcomponents) provided in any one or more of examples 1-66.

Example 68

The method of using any of the devices (or their components and subcomponents) provided in any one or more of examples 1-66.

Example 69

A system including any of the devices (or their components and subcomponents) provided in any one or more of examples 1-66.

Example 70

A kit including any of the devices (or their components and subcomponents) provided in any one or more of examples 1-66.

REFERENCES

The devices, systems, apparatuses, compositions, materials, machine readable medium, computer program products, and methods of various embodiments of the invention disclosed herein may utilize aspects disclosed in the following references, applications, publications and patents and which are hereby incorporated by reference herein in their entirety, and which are not admitted to be prior art with respect to the present invention by inclusion in this section:
1. Allareddy, V., Allareddy, V., and Nalliah, R. P. (2011). Epidemiology of facial fracture injuries. J. Oral Maxillofacial. Surg. 69, 2613-2618.
2. Hwang, K., and You, S. H. (2010). Analysis of facial bone fractures: An 11-year study of 2,094 patients. Indian J Plast Surg 43, 42-48.
3. Mok, D., Lessard, L., Cordoba, C., Harris, P. G., & Nikolis, A. (2004). A review of materials currently used in orbital floor reconstruction. The Canadian Journal of Plastic Surgery, 12(3), 134-140.
4. Left Orbital Fractures I Doctor Stock. (n.d.). Retrieved Apr. 24, 2017.
5. 33. Blowout Fracture of the Orbit I Short Notes in Plastic Surgery. (n.d.). Retrieved Apr. 24, 2017, from https://shortnotesinplasticsurgery.wordpress.com/2013/04/15/735/
6. Vayser, A., Erismann, F., Rimer, D., & Zagatsky, V. (2016, Dec. 6). U.S. Pat. No. 9,510,737—Illuminated suction apparatus.
7. Williams, J. B. (2007, Dec. 11). U.S. Pat. No. 7,306,559—Illuminated surgical retractor.
8. Davis, J. M. (2000, May 9). U.S. Pat. No. 6,059,723—Fiberoptically illuminated tongue depressor.
9. Sayeg, A., & Nemazi, J. E. (2011, May 31). U.S. Pat. No. 7,951,077—Method and instruments for breast augmentation mammaplasty.
10. Florin, R. E. (1971, Dec. 7). U.S. Pat. No. 3,626,471—ILLUMINATED SUCTION BRAIN RETRACTOR.
11. U.S. Pat. No. 6,482,153 B1, Hipps, et al., "Illuminated Surgical Retractor", Nov. 19, 2002.
12. U.S. Pat. No. 6,486,206 B1, Hipps, et al., "Illuminated Surgical Retractor", Oct. 22, 2002.
13. U.S. Pat. No. 8,795,162 B2, Vayser, et al., "Illuminated Suction Apparatus", Aug. 5, 2014.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary.

Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A retractor device for accessing an anatomical region of a subject, said retractor device comprising:
   an elongated member having a distal end and a proximal end with a longitudinal span extending there between along a longitudinal axis, wherein said distal end of said elongated member is configured to access the anatomical region;
   a setoff portion, wherein said setoff portion is a segment of the longitudinal span of said elongated member extending from said distal end in the proximal direction;
   two tubes capable of providing suction, said tubes are disposed along the entire longitudinal span of the said elongated member except for said setoff portion;
   wherein said two tubes are disposed on said elongated member laterally opposed from one another respectively on said longitudinal span;
   each of said two tubes include a distal aperture, wherein said distal apertures of said two tubes are located away from the distal end of said elongated member at said setoff portion and laterally opposed from one another, and said distal apertures are configured to provide the suction to the anatomical region;
   one or more light sources coupled to said elongated member, wherein said one or more light sources are disposed alone the entire longitudinal span of said elongated member, said light sources capable of providing light, and said light sources configured to provide lighting to the anatomical region;
   said one or more light sources are disposed on said elongated member between said two tubes; and
   said elongated member is configured to be bent in one or more positions along the entire longitudinal span in response to manual forces that may be applied by a user onto said elongated member, wherein:
      said elongated member is capable of being bent in a plurality of occurrences in both a longitudinal direction and a lateral direction along the entire longitudinal span into a partial helix shape, wherein:
         said tubes remain operable to provide suction in said one or more bent positions, wherein said tubes are capable of being bent, and
         said light sources remain operable to provide light in said one or more bent positions, wherein said light sources are capable of being disposed along the entire longitudinal span of said elongated member.

2. The retractor device of claim 1, wherein said elongated member is comprised of malleable material possessing a modulus of elasticity or Young's modulus in the range of about 60 GPa to about 250 GPa.

3. The retractor device of claim 1, wherein said elongated member is comprised of malleable material possessing a modulus of elasticity or Young's modulus in the range of about 190 GPa to about 205 GPa.

4. The retractor device of claim 1, wherein said elongated member is comprised of malleable material where said malleable material is defined as being capable of being bent in said one or more positions in response to the manual forces by the user but not substantially bending in response to forces incurred from said elongated member accessing the anatomical region.

5. The retractor device of claim 1, wherein the access of the anatomical region includes drawing back of a subject's bone or tissue.

6. The retractor device of claim 1, wherein said elongated member is capable of elevating tissue of the anatomical region.

7. The retractor device of claim 1, wherein said elongated member is capable of retracting tissue of the anatomical region.

8. The device of claim 1, wherein said elongated member includes a top portion and a bottom portion, and wherein said light sources are coupled to said top portion of said elongated member.

9. The device of claim 1, wherein said elongated member includes a top portion and a bottom portion, and wherein said light sources are coupled to said bottom portion of said elongated member.

10. The device of claim 1, wherein said elongated member includes a top portion and a bottom portion, and wherein said device comprises a plurality of light sources, wherein said light sources are respectively coupled on both said bottom portion and said top portion of said elongated member.

* * * * *